United States Patent [19]
Oswald et al.

[11] Patent Number: 5,190,525
[45] Date of Patent: Mar. 2, 1993

[54] DRUG INFUSION MANIFOLD

[75] Inventors: Timothy J. Oswald, Lincolnshire; Lois L. Caron, McHenry; Mark E. Larkin, Lindenhurst; William L. Rudzena, McHenry; Edward S. Tripp, Park City, all of Ill.

[73] Assignee: Abbott Laboratories, Abbott Park, Ill.

[21] Appl. No.: 816,435

[22] Filed: Dec. 31, 1991

Related U.S. Application Data

[63] Continuation-in-part of Ser. No. 632,254, Dec. 21, 1990, abandoned.

[51] Int. Cl.⁵ ............................................. A61M 37/00
[52] U.S. Cl. ......................................... 604/83; 604/90
[58] Field of Search .................... 604/80, 81, 82, 83, 604/169, 173, 905, 89, 90

[56] References Cited

U.S. PATENT DOCUMENTS

| | | | |
|---|---|---|---|
| 4,063,555 | 12/1977 | Ulinder | 604/83 |
| 4,795,441 | 1/1989 | Bhatt | 604/80 X |
| 4,915,688 | 4/1990 | Bischof | 604/83 |

Primary Examiner—John D. Yasko
Attorney, Agent, or Firm—A. Nicholas Trausch

[57] ABSTRACT

A drug infusion manifold for controlling the infusion of drugs and/or other solutions into an intravenous patient feed line. The manifold includes a housing defining an elongated in-line flow channel that communicates at one end with a carrier fluid inlet line and at the other end with the patient feed line. A plurality of spaced apart drug inlet openings are formed in the housing in communication with the flow channel. Each of the inlet openings is provided with a check valve assembly that includes a valve member defining an inlet socket portion and a valve stem portion that extends into the flow channel. The valve stem portion has a cylindrical side wall that defines an inlet passage that communicates with the socket portion. A plurality of lateral inlet ports extend through the side wall. An elastic sleeve member is received about the valve stem portion in covering relationship with the inlet ports. The valve stem portion is in-line with the flow of carrier fluid through the flow channel.

13 Claims, 3 Drawing Sheets

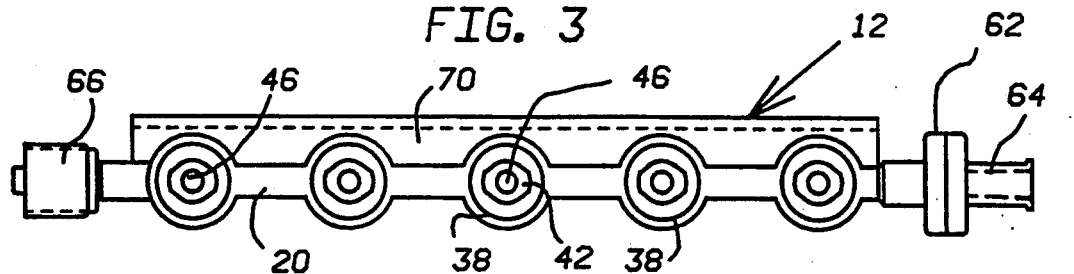
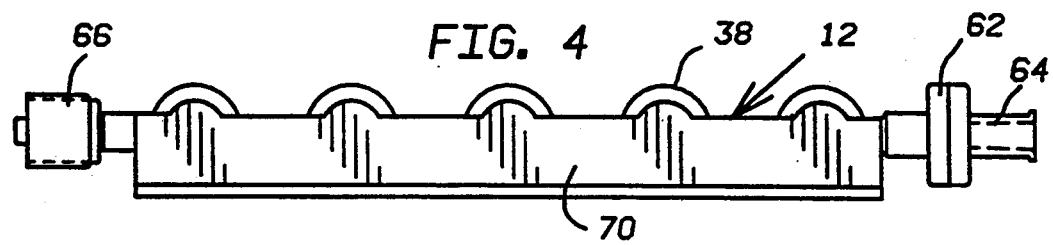
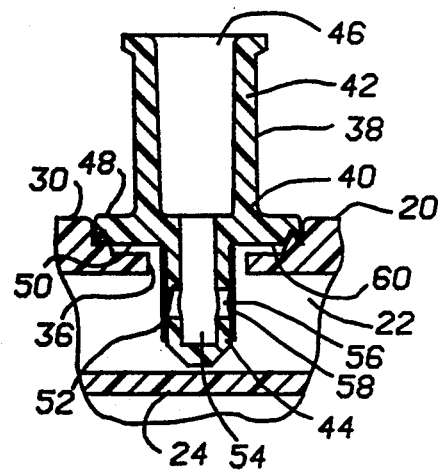
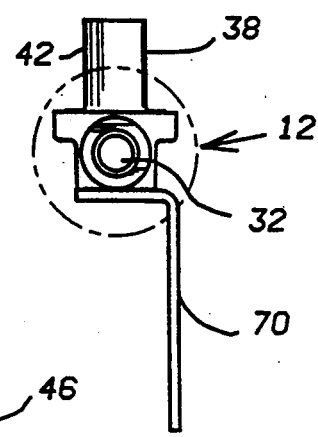
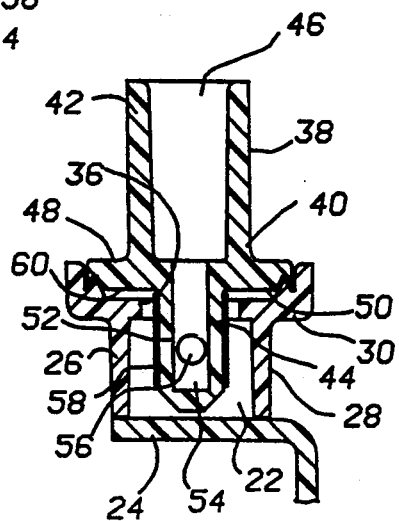

DRUG INFUSION MANIFOLD

BACKGROUND OF THE INVENTION

This application is a continuation in part of U.S. Pat. application Ser. No. 07/632,254 filed on Dec. 21, 1990 now abandoned.

1. Field Of The Invention

This invention relates to a device for controlling the infusion of drugs and/or other solutions. More specifically, the invention relates to an automatic drug infusion manifold that may be used to intravenously administer drugs, such as anesthetic and cardiovascular drugs, without the use of manual switches and which permits gravity delivery of the carrier fluid.

2. Description Of The Prior Art

During surgery, and other medical procedures in the ICU, CCU, ER, it is necessary to deliver different drugs to a patient in a selected and controlled manner. One procedure currently being used to deliver such drugs is by individual syringes. Each syringe is connected to a stopcock which in turn is used with a primary (or patient) IV set. The doctor must manually rotate the knob, handle, control lever, etc. of the stopcock in order to deliver the selected drug to the patient. Depending on the positioning of the stopcocks' knob, etc. and the inside diameter of the IV tubing, there may be a large volume in which different drug residuals may mix. Depending on the particular drugs, such mixing may have adverse effects on the patient, particularly in cardiovascular drug infusion.

Another system that has been used to deliver selected drugs to a patient includes a common manifold device having multiple inlet drug lines that are controlled by individual stopcocks. Similar type devices have been proposed that include various types of valve arrangements in the inlet drug lines to control the infusion of drugs through the inlet drug lines while preventing backflow therethrough. Examples of these types of drug infusion devices are disclosed in U.S. Pat. Nos. 4,666,429, 4,819,684, 4,871,353, 4,908,018 and 4,915,688.

In U.S. Pat. No. 4,346,704 a parenteral solution administration device is disclosed that includes an outer housing defining an outlet tube and an inner tubular support defining an inlet tube. The support has a closed forward end positioned within the outer housing and has lateral apertures through which the bore of the tubular support communicates with the outlet tube. An elastic tube or sleeve surrounds the tubular support in covering relationship with the lateral apertures. The inner tubular support is free of retaining structure at its closed end so as to permit the elastic tube to slide laterally on the tubular support through a limited distance. Upon pressurized fluid flow through the inlet tube, the elastic tube is expanded by pressurized fluid passing through the apertures to permit fluid flow between the tube and tubular support out of both ends of the elastic tube.

In U.S. Pat. No. 4,063,555 a cannula assembly is disclosed that includes a housing defining a fluid flow passage having two fluid inlets and one fluid outlet. One of the fluid inlets is shaped to receive the tip of an injection syringe for introduction of fluid to the inlet. Fluid flow through the inlet is controlled by a check valve housing an elastic tubular valve member closing off outlet openings associated with the check valve. Under sufficient pressure of a fluid in the inlet the tubular valve member deflects outwardly permitting flow through the outlet openings.

There is a need for a drug infusion manifold for controlling the infusion of selected drugs that does not need to be manipulated by hand and does not require manual switching operation. There is a further need for such a device that permits the gravity delivery of the carrier solution. There is also a need for such a device that minimizes the volume of drug residual in the line and yet is still simple in design, reliable and inexpensive to manufacture.

SUMMARY OF THE INVENTION

A non-manual drug infusion manifold is provided that includes a housing defining an elongated in-line flow channel communicating at one end with a carrier fluid inlet line and at the other end with a patient primary IV line. A plurality of spaced apart drug inlet openings are formed in the housing in communication with the flow channel. Each of the inlet openings is provided with a check valve assembly that extends therethrough and permits fluid flow directly into the flow channel of the carrier fluid while precluding fluid flow therefrom.

In accordance with a unique feature of the invention, the check valve assembly includes a valve member defining an inlet socket portion for receipt of the tip portion of a drug-containing syringe, or other drug-containing pump means, thereinto and a generally hollow valve stem portion that extends directly into the flow channel. The valve stem portion is generally cylindrical and has a bore defining an inlet passage that is open at one end and communicates with the socket pocket portion and is closed at the other end and extends into the flow channel. A plurality of lateral inlet ports extend through the side wall defining the inlet passage. A valve sleeve member is received about the valve stem portion in covering relationship with the inlet ports. When the pressure exerted by the fluid from the syringe is sufficient, the sleeve member deflects outwardly permitting fluid flow from the inlet passage of the valve stem portion into the flow channel. The valve stem portion of each of the check valves is in-line with the flow of the carrier fluid through the flow channel.

The bottom portion of the valve stem portion is preferably located a short distance above a flat bottom surface of the flow channel. The valve member defines a shoulder portion in the area where the socket portion meets the valve stem portion. The valve sleeve moves longitudinally along the valve stem during normal operation of the check valve assembly. The movement of the valve sleeve is limited by its contact with the shoulder portion and the bottom surface of the flow channel in a manner that always retains the valve sleeve on the valve stem portion in covering relationship with the inlet ports.

In accordance with other features of the invention, the carrier fluid inlet line is provided with a check valve to preclude backflow of fluid from the flow channel into the carrier fluid inlet line while permitting gravity flow of carrier fluid therethrough. The socket portion of the check valve assembly is preferably configured to receive the male portion of the luer lock fitting. The manifold is preferably formed with an integral support bracket to facilitate gripping and clamping of the device."

DESCRIPTION OF THE DRAWINGS

A better understanding of the drug infusion manifold of the invention will be had by reference to the drawings wherein:

FIG. 3 is a top plan view of the drug infusion manifold shown in FIG. 2;

FIG. 4 is a bottom plan view of the drug infusion manifold shown in FIG. 2;

FIG. 5 is an enlarged sectional view of one of the drug inlet openings;

FIG. 6 is an end view taken along the plane 6—6 in FIG. 2 with the carrier fluid inlet line check valve being shown in phantom lines;

FIG. 7 is a sectional view taken along the plane 7—7 in FIG. 2.

DESCRIPTION OF THE PREFERRED EMBODIMENT

Figure 1:
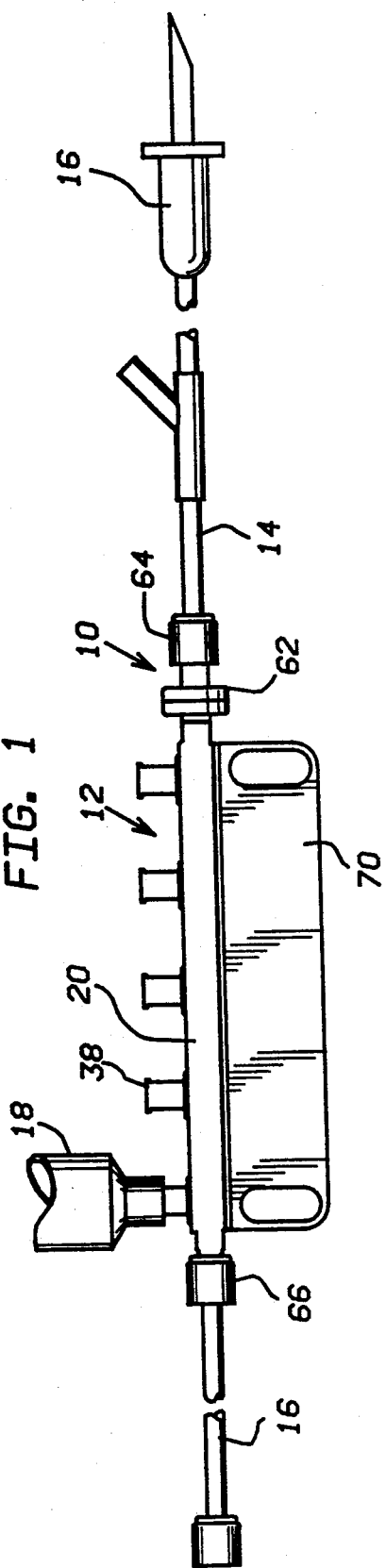
FIG. 1 is an elevational view of a drug administration set utilizing a drug infusion manifold constructed in accordance with the invention.

FIG. 1 illustrates a drug and/or solution infusion system 10 of the type used to administer intravenous anesthetic or cardiovascular drugs and/or solutions into a patient during surgery, ICU, CCU or ER procedures that includes an automatic drug infusion manifold 12 constructed in accordance with the present invention. System 10 includes a drug infusion manifold 12 that is connected to a carrier fluid inlet line 14 having a spike/sight chamber 16 for attachment of the carrier fluid inlet line to an IV set (not shown). A patient feed outlet line 16 delivers the mixture of the carrier fluid and the drug to the patient through a conventional cannula (not shown). A syringe 18 is shown connected to one of the drug inlet openings of the manifold 12. A Y site may be provided in carrier fluid inlet line 14 for infusion of a medicament into the carrier fluid inlet line in a well known manner.

Referring to FIGS. 2-7, a preferred embodiment of an automatic drug infusion manifold 12 incorporating features of the invention includes a housing 20 defining an elongated in-line flow channel 22. Flow channel 22 is generally rectangular in cross section and is defined by a flat bottom wall portion 24, side wall portions 26 and 28 and a top wall portion 30. Flow channel 22 has a first open end portion 32 and a second open end portion 34.

Figure 2:
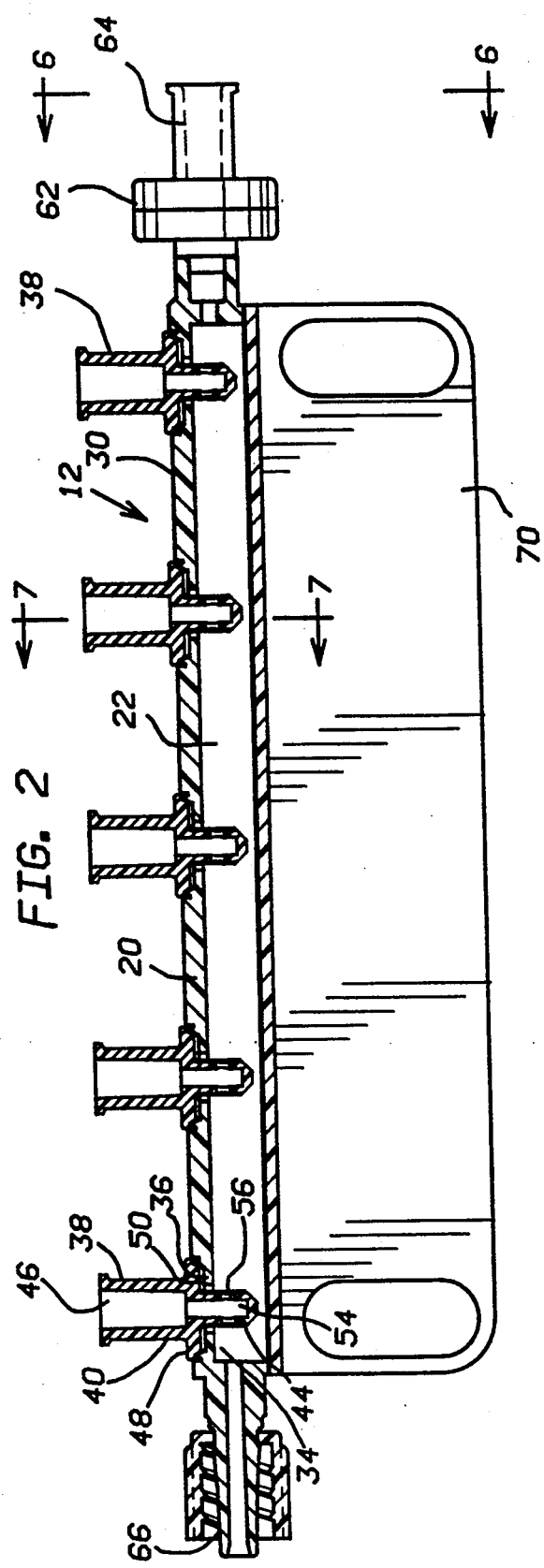
FIG. 2 is an enlarged longitudinal sectional view of the drug infusion manifold of the invention.

As best seen in FIG. 2, a plurality of spaced apart inlet openings 36 extend through top wall portion 30. While the illustrated preferred embodiment has five such openings, it will be understood that it is anticipated that alternative embodiments are envisioned that have either a fewer or a greater number of such openings.

Each of the inlet openings 36 is provided with a check valve assembly 38 for controlling the delivery of drugs into flow channel 22 and precluding the flow of carrier fluid and other drugs from the flow channel. Check valve 38 includes a valve member 40 defining an inlet portion 42 and a valve stem portion 44. Inlet portion 42 defines a socket 46 that is configured to form a female luer lock fitting for receipt of a cooperating male luer lock fitting associated with a drug dispensing syringe, pump, or other drug-containing pump means, in a well known manner. The check valve is preferably formed with an annular flange portion 48 which is received in a cooperating annual recess portion 50 formed in top wall portion 30 around inlet opening 36. Flange portion 48 is preferably ultrasonically welded to the recess portion 50.

Valve stem portion 44 has a cylindrical side wall 52 that defines an inlet passage 54 that is open at one end in communication with socket 46 and is closed at its other end. The valve stem portions 44 extend into flow channel 22 and are in-line with the fluid flow therethrough. The portion of flow passage 22 into which valve stem portions 44 extend are configured to permit carrier fluid flow around the valve stem portions. The bottom of the valve stem portion is positioned a short distance above the inner surface of bottom wall portion 24. A plurality of lateral inlet ports 56 extend through side wall 52 through which the inlet passage 54 communicates with the flow channel 22.

An elastomeric sleeve member 58 is positioned around valve stem portion 44 in covering relationship with ports 56. Sleeve member 58 is preferably an extruded length of silicone tubing. The bottom of valve stem portion 44 is preferably chambered so as to facilitate the assembly of sleeve member 58 around valve stem portion 44. It is anticipated that sleeve member 58 may move longitudinally along the length of valve stem portion 44 during operation of manifold 12. The upward longitudinal movement of the sleeve member is limited as it contacts a shoulder portion 60 defined by flange portion 48 and the downward longitudinal movement thereof is limited as it contacts the inner surface of bottom wall portion 24. The shoulder portion and the inner surface are spaced apart so as to ensure that the sleeve member 58 always remains on stem portion 44 in covering relationship with ports 56.

Figure 8:
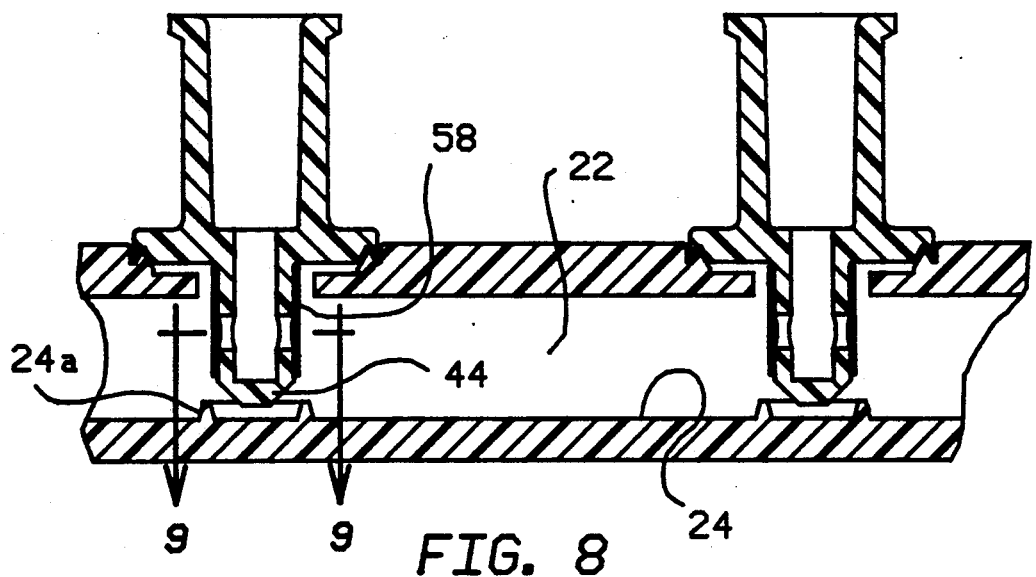
FIG. 8 is an alternative embodiment similar to FIG. 2.
Figure 9:
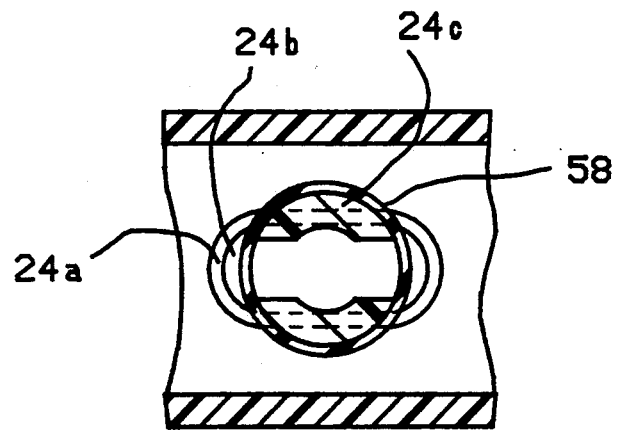
FIG. 9 is a sectional view along plane 9—9 in FIG. 8.

An alternative embodiment is shown in FIG. 8 and 9. An oval shaped, hollow projection 24a is provided on the inner surface of the bottom wall portion 24 centered beneath each stem portion 44.

As seen in FIG. 9, the major axis of the oval is greater than the diameter of the elastomeric sleeve member 58. The minor axis of the oval is less than the diameter of the elastomeric sleeve member 58. Thus, should sleeve member 58 migrate toward the bottom wall portion 24 during use, the travel of the sleeve will be limited by contact with the raised oval portion. Further, fluid flow through the stem during use can exit the bottom of the sleeve and flow into the manifold flow passage 22 through the uncovered ends 24b of the major axis of the oval. Additionally, fluid can flow through the open ends 24c of the sleeve 58 which do not overlap the minor axis of the oval.

This construction relaxes the manufacturing and assembly tolerances required between the shoulder portion and the inner surface of the bottom wall portion 24. Further, the raised oval may promote fluid turbulence and thus fluid mixing in the manifold flow passage during use.

End portion 32 of flow channel 22 is provided with a check valve 62 in fluid communication therewith to preclude the backflow of fluid from flow channel 22 into a carrier inlet line 14 attached thereto while permitting the gravity flow of carrier liquid therethrough into channel 22. Check valve 62 is preferably ultrasonically welded to housing 20 and includes a suitable female luer lock fitting 64 associated therewith for attachment to a cooperating male luer lock fitting associated with the carrier fluid inlet line. Check valve 62 is preferably of the type having a normally closed biased diaphragm that will open with a pressure of 12 inches of water or less.

End portion 34 of flow channel 22 is provided with a male luer lock fitting 66 associated therewith for attachment to a female luer lock fitting associated with the patient inlet feed line 16.

In order to facilitate use of manifold 12 it is provided with a generally flat support bracket member 70 formed integrally with housing 20 for suitably gripping or clamping the manifold in place during use.

The brief discussion of the operation of the above-described preferred embodiment of the invention that follows sets forth the cooperation between the above disclosed structural elements.

In use, the drug infusion system 10 is assembled in such a manner that one end of the carrier fluid inlet line 14 communicates with a supply of carrier fluid, which is typically an IV set having a carrier solution-containing bag elevated on a support pole. Manifold 12 is attached to the other end of the carrier fluid inlet line at fitting 64. The patient feed outlet line 16 is attached to the manifold 12 at fitting 66. Syringes 18 containing preselected drugs and/or solutions are attached to a corresponding socket 46 of a valve assembly 38.

The carrier fluid flows into manifold 12 through open end 32 into flow passage 22, flows around the valve stem portions 44 of the check valves 38, leaves the manifold through open end 34, and is directed through feed line 16 into the patient. At such time as it is necessary to infuse a particular drug or drugs into the patient, the particular drug containing syringe or syringes 18 are depressed directing the drug solution into a passage 54. When the pressure of the drug solution exceeds the cracking pressure of the valve 38, the sleeve member 58 deflects outwardly communicating passage 54 with flow channel 22 through ports 56. In accordance with a preferred embodiment of the invention, the opening pressure required to maintain flow through the valve 38 is preferably from about 1.0 psig to about 8.0 psig, most preferably about 3.0 psig. The flow of drug solution mixes with the carrier solution in channel 22 and the mixture is directed to the patient through line 16. When the pressure of the drug solution is less than the opening pressure of the valve 38, the sleeve member 58 returns to its original position in covering relationship with ports 56 and the flow of drug solution into flow channel 22 is terminated.

After termination of the flow of a particular drug through a corresponding valve 38 into flow channel 22, the residual of that particular drug in the common volume of flow channel 22 is quite minimal and therefore not likely to mix with subsequently added drugs. The in-line flow of carrier liquid around the valve stem portion 44 serves to flush drug residuals therefrom and delivering a total dose of the drug to the patient.

As can be appreciated from the above description of the invention, manifold 12 controls the infusion of selected drugs and does not require a manual switching operation. The manifold 12 also permits the gravity delivery of the carrier solution. The manifold is activated by syringe pressure requiring no manual manipulation, thereby permitting one hand operation. The drugs exit the valve directly into the primary flow line resulting in no pockets of unmixed drugs. The residual volume of drugs above the valves is minimal and there is no flow into pockets associated with adjacent valves.

The check valve prevents retrograde of drug up line of the manifold. The use of the sleeve valves also minimizes contamination associated with manual switches. The manifold also permits use of multiple drug sources such as syringes and IV fluids infused via a positive pressure device, while permitting these drug sources to remain attached without dilution or wicking of drug if no pressure is applied. These advantages are achieved in a manner that is simple in design, reliable in operation, and inexpensive to manufacture.

The foregoing invention can now be practiced by those skilled in the art. Such skilled persons will appreciate that the drug infusion manifold of the present invention is not necessarily restricted to the particular preferred embodiments presented herein. The scope of the invention is to be defined by the terms of the following claims in the spirit and meaning of the preceding description.

What is claimed is:

1. A drug infusion manifold for use in intravenous administration of drugs and/or solutions to a patient, said drug infusion manifold comprising:
   (a) a housing defining an elongated in-line flow channel, said flow channel having a first open end portion for receipt of carrier fluid thereinto and a second open end portion for directing patient feed fluid therefrom;
   (b) a plurality of spaced apart inlet openings formed in said housing in fluid communication with said flow channel; and
   (c) check valve means extending through each of said inlet openings and into said flow channel for directing drugs and/or solutions into said flow channel and precluding fluid flow from said flow channel, said check valve means including a valve member defining an inlet portion for receipt of a drug and/or solution thereinto under pressure and a valve stem portion that extends into said flow channel, said valve stem portion having a side wall that defines an inlet passage that is open at one end in communication with said inlet portion and is closed at the other end, said side wall having at least one lateral inlet port extending therethrough communicating said inlet passage with said flow channel, said valve stem portion having an elastomeric sleeve member received in covering relationship with said inlet port such that when the pressure of the drug and/or solution in said inlet passage exceeds a predetermined level said sleeve member deflects outwardly directing fluid flow from said inlet passage into said flow channel to be transferred to the patient by flow of the carrier fluid.

2. The invention as defined in claim 1 wherein said inlet portion of said valve member defines a socket for receipt of the tip of a drug and/or solution-containing syringe thereinto.

3. The invention as defined in claim 2 wherein said inlet portion defines a female luer fitting for receipt of a cooperating male luer fitting associated with the syringe.

4. The invention as defined in claim 1 wherein said valve member defines a shoulder portion extending outwardly from an upper portion of said valve stem portion and the bottom of said valve stem portion is located a short distance above a bottom surface of said flow channel so as to limit longitudinal movement of said sleeve member on said valve stem portion between said shoulder portion and said bottom surface so as to retain said sleeve member on said valve stem portion in covering relationship with said inlet port.

5. The invention as defined in claim 4 wherein said bottom surface of said flow channel is substantially flat.

6. The invention as defined in claim 1 wherein said first open end portion of said flow channel has a check valve associated therewith to preclude the backflow of fluid from said flow channel therethrough while permitting the gravity flow of carrier fluid therethrough.

7. The invention as defined in claim 1 further including a generally flat support bracket member formed integrally with said housing.

8. The invention as defined in claim 6 wherein said check valve attached to said first open end portion of said flow channel has a female luer fitting associated therewith for attachment to a male luer fitting associated with a carrier fluid inlet line.

9. The invention as defined in claim 1 wherein said second open end portion of said flow channel has a male luer fitting associated therewith for attachment to a female luer fitting associated with a patient feed outlet catheter.

10. The invention as defined in claim 1 wherein said sleeve member is an extruded length of silicone tubing.

11. The invention as defined in claim 1 wherein the bottom end of said valve stem portion is chamfered to facilitate positioning of said sleeve member thereon.

12. The invention as defined in claim 1 wherein said check valve means has an opening pressure in the range from about 1.0 psig to about 8.0 psig.

13. The invention as defined in claim 4 wherein said bottom surface of said flow channel further includes a raised oval portion centered beneath each valve stem portion and having a major axis greater than the diameter of said elastomeric sleeve member and a minor axis less than or equal to the diameter of said elastomeric sleeve portion.

* * * * *